US00PP26702P3

(12) United States Plant Patent
Kapiteijn

(10) Patent No.: US PP26,702 P3
(45) Date of Patent: May 3, 2016

(54) ***ZANTEDESCHIA* PLANT NAMED 'CAPTAIN SOLO'**

(50) Latin Name: *Zantedeschia sprengeri*
Varietal Denomination: CAPTAIN SOLO

(71) Applicant: Antonius Simon Johannes Kapiteijn, Anna Palowna (NL)

(72) Inventor: Antonius Simon Johannes Kapiteijn, Anna Palowna (NL)

(73) Assignee: Kapiteyn Breeding BV (NL)

( * ) Notice: Subject to any disclaimer, the term of this patent is extended or adjusted under 35 U.S.C. 154(b) by 130 days.

(21) Appl. No.: 14/120,391

(22) Filed: May 16, 2014

(65) Prior Publication Data

US 2015/0334909 P1 Nov. 19, 2015

(51) Int. Cl.
*A01H 5/02* (2006.01)

(52) U.S. Cl.
USPC ..... Plt./490

(58) Field of Classification Search
USPC ..... Plt./490
See application file for complete search history.

*Primary Examiner* — Anne Grunberg
(74) *Attorney, Agent, or Firm* — Cassandra Bright

(57) ABSTRACT

A new and distinct *Zantedeschia* cultivar named 'CAPTAIN SOLO' is disclosed, characterized by yellow inflorescence, flowers occurring above the leaves and a short plant height. The new variety is commercially suitable for indoor plant production.

1 Drawing Sheet

Latin name of the genus and species: *Zantedeschia sprengeri.*

Variety denomination: 'CAPTAIN SOLO'.

BACKGROUND OF THE INVENTION

The new cultivar is a product of a planned breeding program. The new variety originated from a cross pollination, made by the inventor in 2008, of a proprietary seed parent identified as '04453(scp.8534-9b)' and a proprietary pollen parent identified as '06330(apm.1198)', both *Zantedeschia sprengeri.*

The new variety was discovered and selected by the inventor, Anthonius Simon Johannes Kapiteijn, a citizen of the Netherlands, in June of 2010 in a group of seedlings resulting from the crossing. The new cultivar was found in a commercial greenhouse belonging to the inventor in Anna Paulowna, the Netherlands.

Asexual reproduction of the new cultivar 'CAPTAIN SOLO' was first performed by tissue culture at a commercial laboratory in the Netherlands in 2011. Tissue cultured plants were subsequently grown out to produce tubers. 'CAPTAIN SOLO' has been reproduced by both tissue culture and tubers and has shown that the unique features of this cultivar are stable and reproduced true to type.

SUMMARY OF THE INVENTION

The cultivar 'CAPTAIN SOLO' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'CAPTAIN SOLO'. These characteristics in combination distinguish 'CAPTAIN SOLO' as a new and distinct *Zantedeschia* cultivar:

1. Yellow inflorescence.
2. Flowers occurring above leaves.
3. Short plant height.

PARENT COMPARISON

Plants of the new cultivar 'CAPTAIN SOLO' are similar to plants of the seed parent variety, in most horticultural characteristics, however, plants of the new cultivar produce yellow inflorescence, whereas the seed parent produces an orange inflorescence.

Plants of the new cultivar 'CAPTAIN SOLO' are similar to plants of the pollen parent variety, in most horticultural characteristics, however, plants of the new cultivar produce yellow inflorescence, whereas the pollen parent produces an orange inflorescence.

COMMERCIAL COMPARISON

Plants of the new cultivar 'CAPTAIN SOLO' are similar to plants of the unpatented variety, *Zantedeschia sprengeri* 'Golden Nugget', unpatented in most horticultural characteristics, however, plants of the new cultivar are shorter in height, produce more flowers and a rounder inflorescence shape than 'Golden Nugget'

Plants of the new cultivar 'CAPTAIN SOLO' are also similar to plants of the unpatented variety, *Zantedeschia sprengeri* 'Serrada', unpatented in most horticultural characteristics, however, plants of the new cultivar are shorter in height, produce a darker yellow flower color and a rounder inflorescence shape than 'Serrada'.

BRIEF DESCRIPTION OF THE PHOTOGRAPH

The accompanying photograph in FIG. 1 illustrates in full color typical plants of 'CAPTAIN SOLO' grown in a greenhouse in Anna Paulowna, the Netherlands. The plants are approximately 2 year old, shown growing in 14 cm pots. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'CAPTAIN SOLO' plants grown in a climate controlled greenhouse in Anna Paulowna, the Netherlands. Temperatures ranged from 18° C. to 22° C. day to 12° C. to 16° C. at night. No artificial light or photoperiodic treatments were given to the plants. The following chemical treatments were used; GA 3 (Berelex) growth regulator. Before planting growth retardant (padobutrazol) at a dose of 1 ppm. Measurements and numerical values represent averages of typical plant types.

Botanical classification: *Zantedeschia sprengeri* 'CAPTAIN SOLO'.

PROPAGATION

First propagation method: Tissue culture.

Type of propagation typically used: Tuber division.

Time to initiate roots: Approximately 10-30 days at approximately to 18-22 C.

Root description: Moderately dense, moderately branched, slightly fibrous, non-fleshy colored white; near RHS NN155C.

Time to produce rooted plantlet: Approximately 10-30 days at approximately 18 to 22° C.

PLANT

Growth habit: Upright, clumping, shoots grow directly from base.

Plant shape: Broad obovate.

Height: Approximately 28.8 cm to top of highest leaf, Approximately 32.4 cm to top of highest inflorescence.

Plant spread: Average: 32.4 cm.

Normal pot size: 14 cm pots and larger.

Growth rate: Moderate.

Branching characteristics: No branching, clump forming. Leaves emerge directly from base of plant.

Number of clumps per plant: Average: 8.

Number of leaves per clump: Approximately 3.

Number of leaves per plant: Approximately 24.

Age of plant described: Approximately 24 months.

FOLIAGE

Leaf:

*Arrangement*.—Equitant.

*Average length* (*excluding petiole*).—Approximately 15.9 cm.

*Average width*.—Approximately 9.4 cm.

*Shape of blade*.—Ovate to broad ovate.

*Aspect*.—Leaves in an average angle of 45° (varying between horizontal (=0°) and 90°).

*Apex*.—Acute with a mucronate tip.

*Base*.—Cordate.

*Margin*.—Entire, strongly undulate.

*Texture of top surface*.—Glabrous, very slightly glossy.

*Texture of bottom surface*.—Glabrous, very slightly glossy.

*Color*.—Young foliage upper side: A color between Green; 137B and 143A but slightly darker, irregularly flecked with transparent Green-white; near RHS 157C and 157D. Young foliage under side: Green; near RHS 137C, irregularly flecked transparent Green-white; near RHS 157C to 157D. Mature foliage upper side: Green; near RHS N137C, irregularly flecked transparent White; near RHS NN155C. Mature foliage under side: Green; near RHS 137B, irregularly flecked transparent White; near RHS NN155C.

Venation:

*Type*.—Pinnate.

*Venation coloration upper side*.—Green; near RHS 137B.

*Venation coloration under side*.—Green; near RHS 143C.

Petiole:

*Length*.—Approximately 12.7 cm.

*Width*.—No geniculum visible, approximate width at distal end of petiole: 0.6 cm. Proximal end Approximately 1.4 cm.

*Color*.—Green in between near RHS 143B and 143C, base strongly tinged brown: near Brown RHS 200A to 200C.

*Strength*.—Moderate.

Wing:

*Length*.—Approximately 6.9 cm.

*Width*.—Approximately 1.1 cm.

*Color*.—Under (outer) side yellow-green; near RHS 144B to 144C, moderately tinged brown; near RHS 200B and 200C. Upper (inner) side yellow-green; near RHS 147D.

INFLORESCENCE

Arrangement: Individual inflorescences grow from the centre of each clump.

Flowering habit: Once a year, from late spring into summer.

Quantity of spathes per plant: On average: 12 fully open spathes in good condition.

Natural flowering season: Spring into summer.

Time to flowering: Approximately 8 months from propagation.

Fragrance: None.

Self-cleaning or persistent: Persistent.

Flower longevity: Flowers stay in good condition approximately 3 weeks on the plant.

Spathe:

*Aspect*.—Upright, straight on top of peduncle.

*Length*.—Approximately 8.5 cm.

*Width*.—Approximately 6.3 cm.

*Shape*.—Broad ovate to near orbicular, base folded around spadix.

*Margin*.—Entire, revolute slightly undulate.

*Apex*.—Aristate.

*Base*.—Broad cuneate, circular (folded around spadix).

*Color*.—Front when opening: Yellow; near RHS 6A, base tinged yellow-green; near RHS 150C and 150D. Back when opening: Yellow; near RHS 9B, lower half tinged yellow-green; near RHS 144B, tip green; near RHS 143A. Front when mature: Yellow; near RHS 12A, base lighter; near RHS 8A, outer tip green; near RHS 143A. Back when mature: Yellow; near RHS 12A, base tinged green; near RHS 143B to 143C, main vein and tip green; near RHS 143A and 143B. Fading to: Front fading yellow-orange; near RHS 14B, back fading yellow-green; near RHS 144B.

Spadix:

*Shape*.—Columnar.

*Tip*.—Obtuse.

*Base*.—Obtuse.

*Length*.—Approximately 4.4 cm.

*Width*.—Approximately 1.0 cm.

*Color*.—When opening: Lower 40% (female flowers) yellow-green; near RHS 145C to 145D, upper 60% (male flowers) yellow; near RHS 13A. Mature: Near RHS Lower 40% (female flowers) yellow-green; near RHS 144C to 144D, upper 60% (male flowers) yellow-orange; near RHS 15A to 15B.

*Quantity of flowers per spadix*.—Approximately 35 female flowers (consisting of a single style and ovary) approximately 400 male flowers (consisting of anthers only).

*Spadix flower arrangement*.—Female flowers (consisting of a single style and ovary) arranged at the base of the spadix (lower 40%), male flowers (consisting of anthers only) arranged above the female flowers (upper 60% of the spadix).

*Spadix flower diameter*.—Female flowers (consisting of a single style and ovary) Approximately 0.35 cm, male flowers (consisting of anthers only) approximately 0.1 cm.

*Spadix flower depth*.—Female flowers (consisting of a single style and ovary) Approximately 0.2 cm, male flowers (consisting of anthers only) approximately 0.75 cm.

Peduncle:

*Length*.—Approximately 19.9 cm.

*Diameter*.—Approximately 0.7 cm.

*Color*.—Green; near RHS 143C.

*Strength*.—Moderate.

REPRODUCTIVE ORGANS

*Anther color*.—Near RHS Yellow-orange 15A to 15B.

*Pollen color*.—Near RHS White 155A.

*Stigma color*.—Near RHS Yellow-Orange. 11A.

*Ovary color*.—Near RHS Yellow-green 144C to 144D.

OTHER CHARACTERISTICS

Disease/pest resistance: Typical of *Zantedeschia*.

Temperature tolerance: The new cultivar is a typical *Zantedeschia*, tolerant of temperatures approximately 10° to 28° C.

Fruit/seed production: Not observed.

What is claimed is:

1. A new and distinct cultivar of *Zantedeschia* plant named 'CAPTAIN SOLO' as herein illustrated and described.

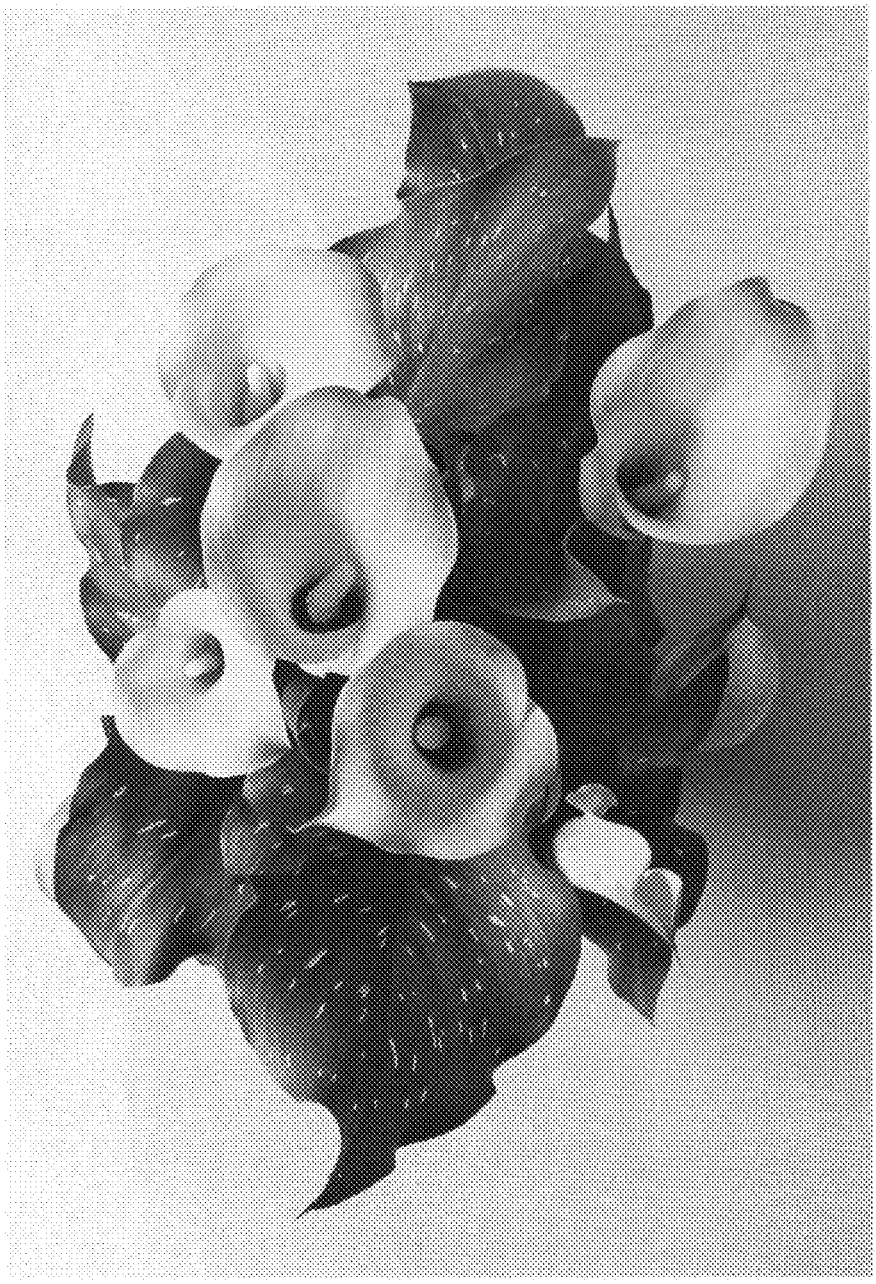

* * * * *